(12) United States Patent
Nobbe (10) Patent No.: US 7,641,625 B2
(45) Date of Patent: Jan. 5, 2010

(54) COMPOSITE LIMB GUARD

(76) Inventor: Ralph W. Nobbe, 3010 State St., Santa Barbara, CA (US) 93105

(*) Notice: Subject to any disclaimer, the term of this patent is extended or adjusted under 35 U.S.C. 154(b) by 576 days.

(21) Appl. No.: 11/149,116

(22) Filed: Jun. 8, 2005

(65) Prior Publication Data

US 2005/0278039 A1 Dec. 15, 2005

Related U.S. Application Data

(60) Provisional application No. 60/579,790, filed on Jun. 14, 2004.

(51) Int. Cl.
*A61F 5/00* (2006.01)
*A61F 13/00* (2006.01)
*A61F 2/78* (2006.01)
*A61F 2/80* (2006.01)
*A61F 5/28* (2006.01)

(52) U.S. Cl. .............. 602/63; 602/23; 602/60; 602/62; 602/72; 623/33; 623/32; 623/34; 623/35; 623/36; 128/99.1; 128/105.1; 128/106.1; 128/107.1

(58) Field of Classification Search .......... 602/63, 602/23, 60, 62, 72; 623/32–36; 128/99.1, 128/105.1, 106.1, 107.1
See application file for complete search history.

(56) References Cited

U.S. PATENT DOCUMENTS

| | | | |
|---|---|---|---|
| 4,479,272 A | 10/1984 | Beldzisky | |
| 4,842,608 A | 6/1989 | Marx et al. | |
| 4,923,474 A | 5/1990 | Klasson et al. | |
| 5,211,667 A | 5/1993 | Danforth | |
| 5,529,575 A * | 6/1996 | Klotz | 623/33 |
| 5,571,209 A | 11/1996 | Brown, Sr. | |
| 5,651,792 A * | 7/1997 | Telikicherla | 623/36 |
| 5,728,165 A | 3/1998 | Brown, Sr. | |
| 5,888,231 A | 3/1999 | Sandvig et al. | |
| 2005/0240283 A1* | 10/2005 | Kania | 623/36 |

OTHER PUBLICATIONS

"Adjustable Postoperative, Protective and Preparatory System For Transtibial Amputees", *Flo-Tech APOPP*, pp. 1-4 (2004).
"APOPPS Abstract", *Flo-Tech APOPPS*, pp. 1-5 (2004).

* cited by examiner

*Primary Examiner*—Tarla R Patel
(74) *Attorney, Agent, or Firm*—Koppel, Patrick, Heybl & Dawson; Michael J. Ram (57) ABSTRACT

A post amputation limb protection to be applied to newly or recently amputated transtibial, transradial or transfemoral residual limbs comprises an inner soft liner for placement on and around the limb above the end of the stump, an end pad for placement over the stump, a shell for placement over the end pad and inner soft liner, medial and lateral struts for placement along the length of the limb over the inner soft liner, attachment structures on the various components and strap closures for securing the components to the limb, and a waist belt and suspensor, for attachment to the assembly to keep the assembly in place.

9 Claims, 5 Drawing Sheets fig. 3 fig. 4 fig. 5A fig. 7A

COMPOSITE LIMB GUARD

This application claims benefit of U.S. Provisional Application Ser. No. 60/579,790, filed Jun. 14, 2004.

This application is directed to a post amputation limb protection system and more particularly a protection system to be applied to newly or recently amputated transtibial, transradial or transfemoral residual limbs.

BACKGROUND

The incidence of trauma to newly amputated limbs is significant and can be debilitating. This population is primarily the diabetic, dysvascular and/or patients otherwise in generally poor health. These patients are at great risk of falling and of delayed wound healing. They may never become prosthetic candidates, particularly if they fall onto their residual limb and re-open the surgical wound.

Prior devices for post operative application include:

a) U.S. Pat. No. 5,211,667, issued to Michael Danford, shows a prosthesis for protecting a residual limb. The device comprises an upper shell lined with a soft material contoured to match the residual limb and a lower shell telescoping over the upper shell. The assembly includes slots through both shells to receive an elongated strap on the end of the sock covering the stump and fasteners on the external surface of the lower shell for attachment of the strap to the lower shell. Danforth prosthetics of Florida (now Otto Bock) offers the Danforth D-Pass stump protector, believed to be the device shown in the '667 patent. This product includes a molded thermoplastic exterior shell. It is available in both left and right version, that are not interchangeable, and 7-10 sizes of each are required to meet the needs of the variety of patients. It is not provided with a waist belt suspension system nor does it include a reticulated end pad for cushioning the surgical wound.

b) Non-Weight bearing dressings—WU dressing or non-weight bearing removable rigid dressings ("removable" applies to a specific casting technique and does not refer to a device which can be reapplied after removal) is a cast application technique, not a commercially available product. These are primarily casts that are applied directly to the residual limb. Casting material, readily available in most medical facilities, provides a rigid shell. However it can be tricky to apply in a manner that will prevent pressure sores on bony prominences. They are not easily removable for wound and dressing changes. If they are removed or inadvertently slide off, re-application can cause wound trauma. Skilled operators are also required for the application of these devices so that a tourniquet effect is not created proximally. Additionally, they can not be readily post-formed to accommodate change or to make adjustments. There is also a risk of skin breakdown when a cast-like removable rigid dressing is used.

c) Flo-tech manufactures a knee extension, post amputation protective device known as APPOPS for postoperative knee immobilization. This device indicates it is covered by U.S. Pat. Nos. 5,571,209 and 5,728,165 issued to Robert Brown and assigned to Flo-Tech Orthotic & Prosthetic Systems. These patents show a post operative protective socket for transtibial amputees. The device labeling includes a single piece semi-rigid plastic structure, which includes a cup-shaped base, into which the stump is placed, with the plastic structure partially surrounding the limb above the amputation site. Circumferential cuffs are attached to the rear surface of the shell for securing the hard shell to the stump. Because of its construction, multiple sizes are required for different patients and different assemblies are required for left or right application. It is also indicated that it can be used prior to progression into a weight bearing prosthetic system.

SUMMARY

The limb guard assembly described herein, incorporating features of the invention, can be broadly used but is particularly applicable to high risk patients. It can also been utilized for traumatic injuries in younger and pediatric populations. Its primary intended use is in a non-weight bearing, post-operative protocol to maintain the knee in full extension, allow full hip range of motion and provide protection against trauma to the new surgical site during transfers and mobilizations of the new amputee. It provides a protective environment to the newly amputated residual limb and can be easily removed for wound inspection and dressing changes. It may be worn over surgical dressings, and is sized so that it can accommodate variations in dressing sizes and can be worn over prosthetic socks, Ace bandages or prosthetic shrinker socks. It has been found that three different sizes will generally accommodate the majority of left and right transtibial residual limbs but smaller and larger sizes can be provided. This assembly provides a low cost, easy to apply protective structure to prevent or reduce trauma following surgery. A limb guard incorporating features of the invention can be used universally for left or right sided applications. Other embodiments of similar construction are intended for transfemoral application, differing primarily in the outer appearance and size of component parts.

In a preferred mode the limb guard is applied in the early post operative phase. It can be applied directly in the operating room but most frequently is applied 2-5 days post-operatively prior to first mobilization after amputation surgery. While it may be applied over surgical dressings, it is usually applied following the first postoperative dressing change, which typically reduces the bulk of the dressing. This eliminates the potential need to "refit" when the initially bulky dressing is reduced. Typically, application over a prosthetic sock, which is applied over any surgical dressings, is recommended. This allows easy subsequent removal without disruption of the surgical dressing. The limb guard is preferably worn at least at night while sleeping and during active waking hours. In particular, the device should be worn during transfers from bed to wheelchair or wheelchair to stationary chairs. This minimizes the risks of wound trauma during these transfers or the potential slip and fall during these transfers. Night time use is also important as new amputees frequently forget the amputation has occurred and attempt to get up independently in the middle of the night, fall and cause major wound traumas. Of primary concern, a fall could cause the wound to re-open, which can significantly delay healing and increase the risk of infection, which in turn might require revision of the amputation to a higher surgical level, such as above knee or knee disarticulation amputation. The same design can be used, in smaller sizes, for pediatric application or lesser extent upper limb amputees. When applied following a transtibial amputation it maintains the knee in extension reducing or preventing knee contractures. While primarily designed for short-term application of approximately 4-8 weeks to allow primary wound healing to occur, extended use is also contemplated.

The limb guard incorporating features of the invention can be provided in a range of sizes and the components can be provided as permanent attachments so nursing or other allied health staff can easily disassemble them. Some of the components could be fabricated with thinner or lighter materials, reducing weight and bulk.

BRIEF DESCRIPTION OF THE DRAWINGS

The foregoing and other features and advantages of devices incorporating features of the invention will be more fully understood from the following detailed description and illustrative embodiments, taken in conjunction with the drawings in which:

FIG. 5b is a front perspective view of a second embodiment of liner of FIG. 5a.

DETAILED DESCRIPTION

Referring to FIGS. 1-7, a first embodiment of a limb guard assembly 10, incorporating features of the invention, comprises an inverted "Y" suspensor 12 which is attached, at its lower end, to two conformable lateral struts 14 and, at its upper end, to a waist belt suspensor 16. The lateral struts 14 are in turn attached, preferred using Velcro® hook and loop connectors, to the outer surface of a soft inner liner 18 and to the distal rigid shell 20. The soft inner liner 18 is wrapped circumferential around the remaining portion of the limb above the amputation site. Placed in the distal rigid shell 20 adjacent the surgical wound and immediately adjacent the lower end of the inner liner is a reticulated end pad 22, providing an inner soft lining between the skin of the limb and the struts 14 and rigid shell 20.

Figures 1, 2:
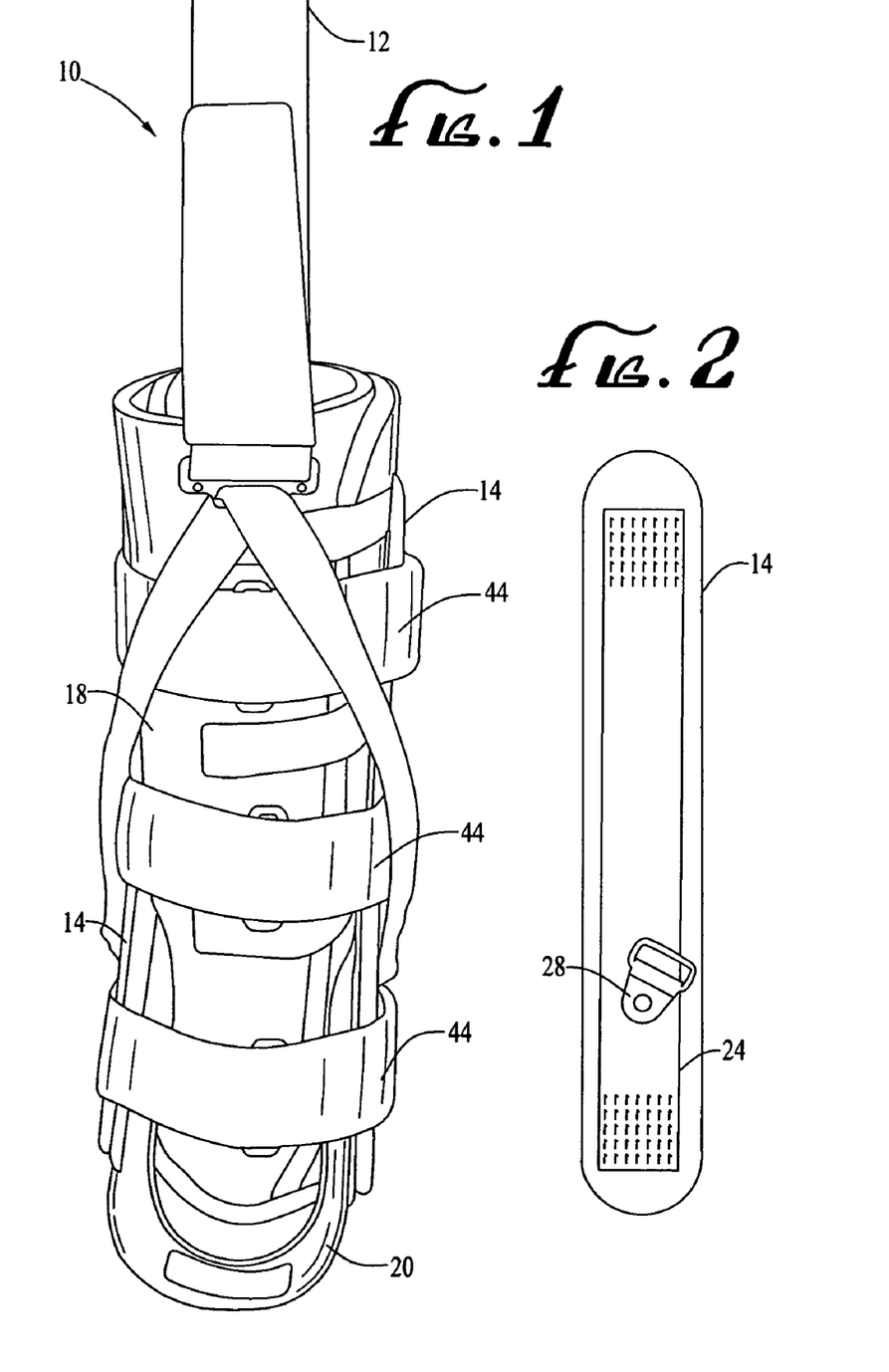
FIG. 1 is a front assembled view of a limb guard assembly incorporating features of the invention and showing various components of the assembly
FIG. 2 shows the lateral struts used in the assembly of FIG. 1.

As best shown in FIG. 2, the lateral struts 14 are formed from a flat, stiff material such as ⅛ to 3/16 thick thermoplastic copolymer. They are approximately from about 1" to about 2" wide, preferably 1½" wide and approximately 18" long, the width and length being chosen to best adapt to the size of the limb being fitted. A length of Velcro® hook fasteners 24 are applied to both sides along a substantial length of the strut, with one side being provided for adhesion directly onto the inner liner 18 and the second side for receiving circumferential securing straps 44. A "D" ring 28 is pivotably attached to allow for attachment of the inverted "Y" suspensor 12. In a preferred arrangement the D ring is located above the patella once assembled.

Alternatively, the struts 14 can be constructed of a malleable metal such as aluminum with Velcro fasteners attached thereto so that the struts can be contoured to the residual limb to accommodate angulations. Still further, the struts 14 may be constructed of a composite material to reduce the weight and bulk. Alternative plastic materials include, but are not limited to, ABS, Kydex® or polyethylene.

Figure 3:
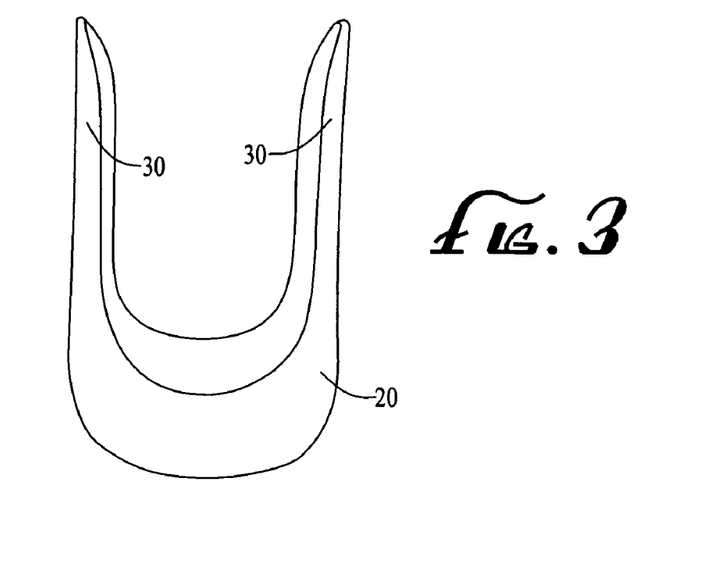
FIG. 3 is a front perspective view of a distal rigid shell used in the assembly of FIG. 1.

FIG. 3 shows an embodiment of a distal rigid shell 20. The distal rigid shell 20 is formed in a conical shape larger than but generally matching the contour of a limb stump following amputation. The shell 20 is preferably molded from polyethylene, polypropylene or thermoplastic copolymer materials having similar physical properties. The molded shell 20 is generally between 0.125 and 0.175 inches thick with lateral projections 30 extending upwardly approximately 5 inches. The rigid shell depth (the lower area which receives the stump) is approximately 1.5 inches along its anterior and posterior margins. Both the inner and outer surface of the lateral extensions include Velcro® compatible material (not shown) so that components placed within or external to the shell 20 can be attached to the shell 20 using the Velcro® hook and loop fasteners. The extensions 30 on the rigid shell 20 are flexible to allow contouring to the residual limb. As with the struts, the shell 20 can also be fabricated from a variety of materials including composites, aluminum, or other thermoplastic polymers. The inner dimensions of the lower portion of the rigid shell determines the sizing of the limb guard being required as the diameter of the residual limb or the amputated stump (with dressing or sock) is received within that lower portion. Generally, a diameter from about 3" to about 8" is adequate with most patients being properly fitted with a 4" 5" or a 6" diameter rigid shell. Smaller sizes accommodate some upper limb amputations and juvenile or pediatric applications; sizes larger the 6" are required for obese or very athletic patients with muscular limbs.

Figure 4:
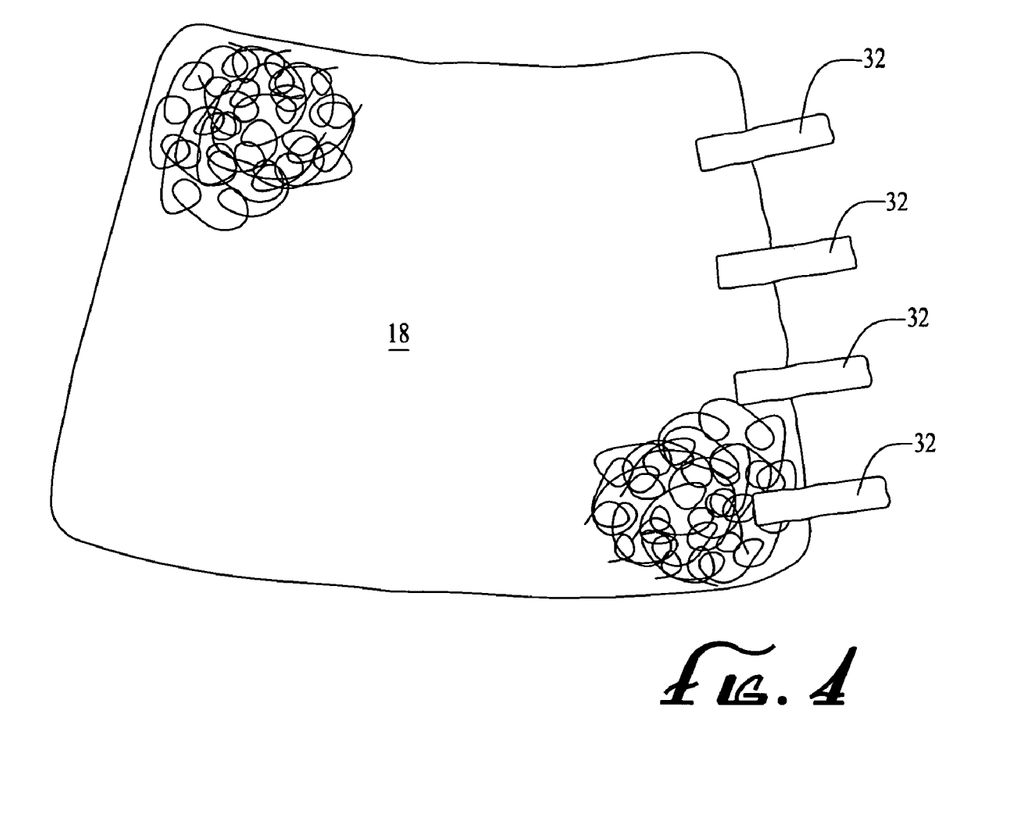
FIG. 4 is a front view of an inner soft liner used in the assembly of FIG. 1.

The inner soft liner 18 shown in FIG. 4 is a foam and/or fabric wrap system that has a Velcro compatible fabric outer surface. It is preferably formed of a reticulated foam sandwich type construction, approximately ⅜ of an inch or 1 centimeter in thickness. The wrap 18 is constructed such that it can wrap around the residual limb and be easily customized to fit if necessary. Velcro® hook tabs 32 are attached to one end so that, once wrapped around the residual limb they can be adhered to the outer surface of the wrap 18. When the limb guard assembly is removed it can be washed and reapplied to the limb. Alternative materials for the inner liner 18 include molded thermoplastic foam, such as Plastizote®, Aliplast® or EVA or other similar functioning materials. However, these alternative materials may require custom molding and forming to the patient, thus increasing the fitting time. Other similar foam or fabric materials can be used, allowing thicker or thinner inner liners to be utilized.

Figure 5A:
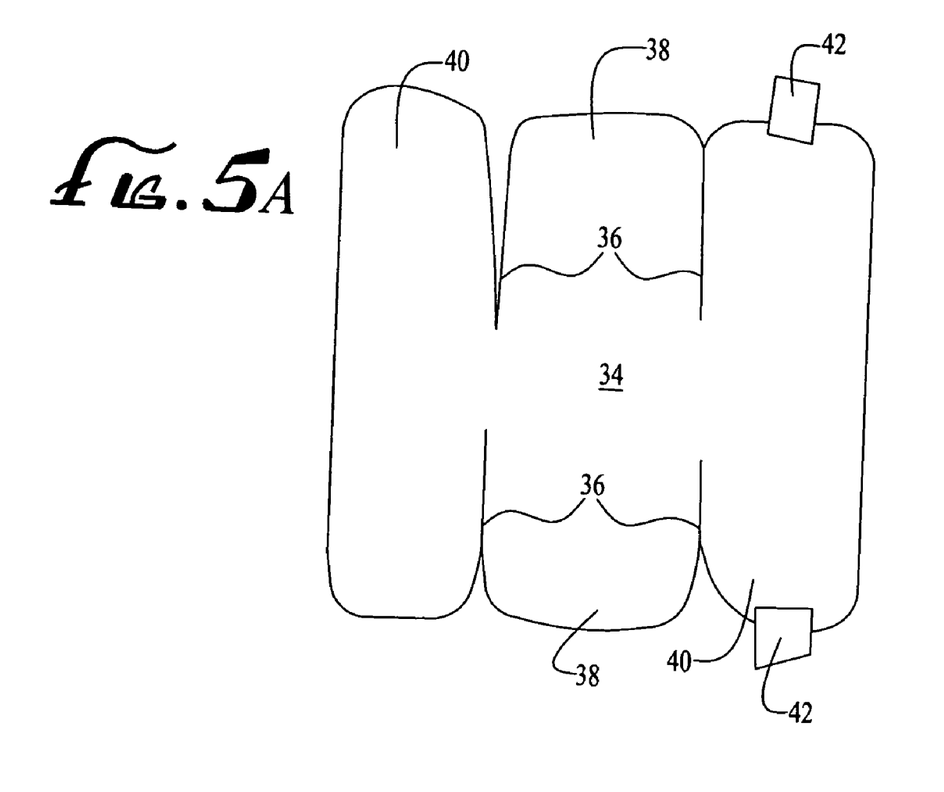
FIG. 5a shows an end liner flattened prior to placement on the limb before application of the assembly of FIG. 1.

FIG. 5a shows one embodiment of a soft end liner 34. The end liner 34 consist of a flat component that has trifurcations 36 on either sides. This allows the middle tab 38 to be folded up around the residual limb. The end tabs 40 are then folded around on either side and held in place with Velcro tabs 42 onto the inner liner 18 providing a smooth inner surface. The end liner 34 can be cut and trimmed easily to accommodate the distal residual limb shape. Like the inner liner, the soft end liner 34 can alternatively be fabricated from Plastizote® or other similar materials but would require custom fabrication to do so. Alternative material for this inner liner 34 could be a molded thermoplastic foam such as Plastizote® (an inert, closed-cell, cross-linked polyethylene foam), Aliplast® (a cross-linked, polyethylene foam) or EVA. Other similar foam type materials can be used, which may allow either thicker or thinner end liners to be utilized. The limb guard assembly 10 may be applied to patients without using this end liner 34, particularly on the larger residual limbs where its use is optional and not required. This is a clinical judgment to be determined by the professional doing the application.

Figure 5B:
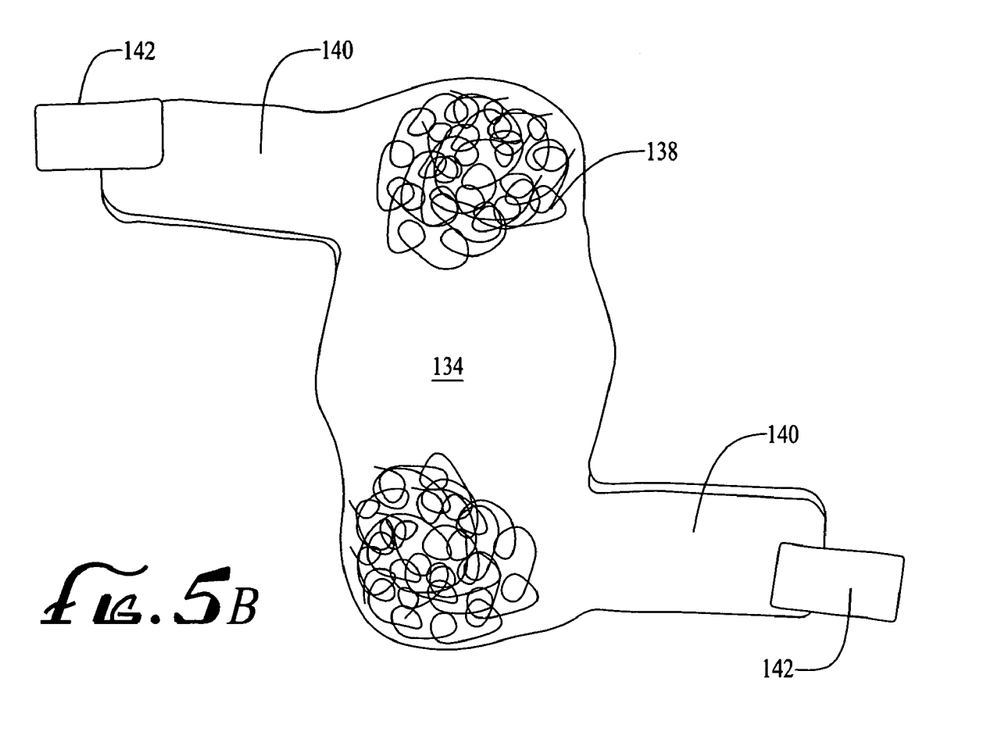

FIG. 5b is a second embodiment of the soft liner 134. This embodiment has a middle portion 138 which is folded up around the residual limb tabs 140, are then wrapped around either side of the limb and secured using Velcro® tabs 142.

Figure 6:
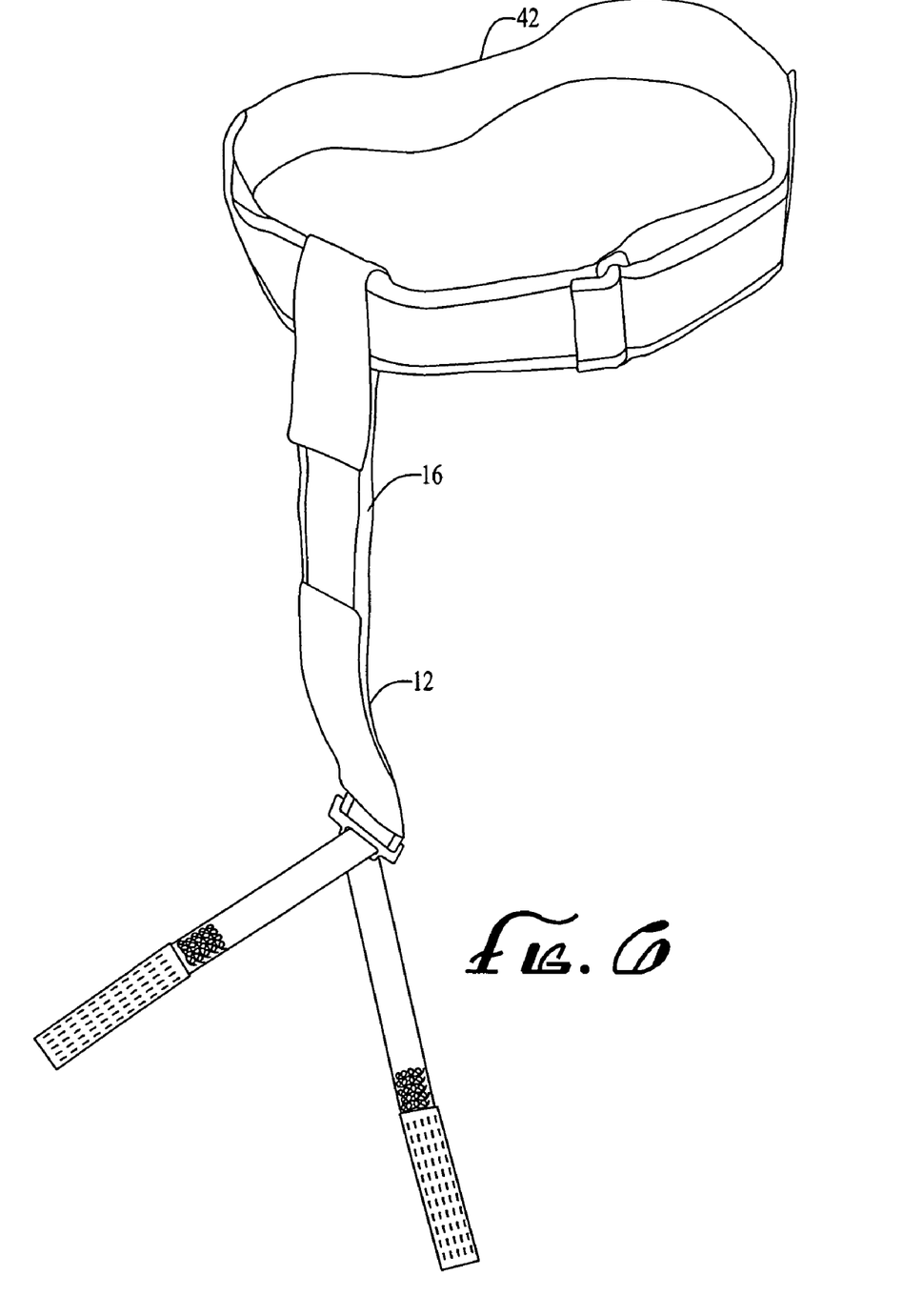
FIG. 6 is a front perspective view of a waist belt and "Y" suspensor used to hold up the assembly of FIG. 1

An embodiment of the waist belt 42 with the inverted wide suspensor 16 is shown in FIG. 6. The waist belt portion 42 is made long enough so that it can be used on a broad range of patients, typically 46-48 inches long. It is intended to be universal in size and can be used to hold the limb guard applied to either right or left side amputations. This is accomplished by providing the inverted "Y" suspensor 12 with Velcro fasteners for attachment onto the circumferential waist belt at a desired location on the left or right side. The waist belt may be attached to the waist of the user by any of the numerous buckles or attachment means used to secure belts. The inverted "Y" suspensor 12 provides direct vertical suspension of the limb guard assembly 10. It does not create an abduction or abduction component at the hip and provides rotary stability as well. It also serves to maintain the knee in extension. The waist belt is also of sufficient length for a smaller individual to use as a shoulder suspensor over the contra-lateral shoulder. An extension (not shown) can also be added so that the belt can be used by obese individuals in an over-the-shoulder arrangement.

Alternatively, various waist belts and prefabricated pelvic belt/hip attachments can be utilized. One skilled in the art will recognize that, based on the teachings herein, various different belt arrangements can be used. Alternative constructions include alteration of the width and length of the waist belt to accommodate varying sizes. The waist belt can also be tailored and contoured if desired.

Figure 7A:
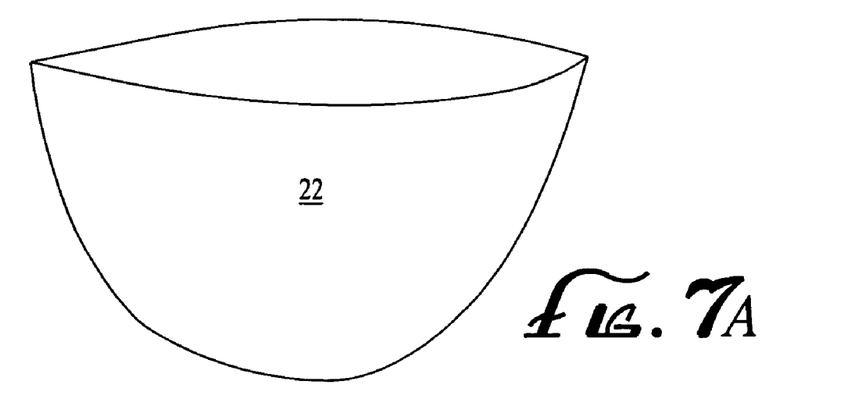
FIG. 7a is a front perspective view of a reticulated end pad used in the assembly of FIG. 1.
Figure 7B:
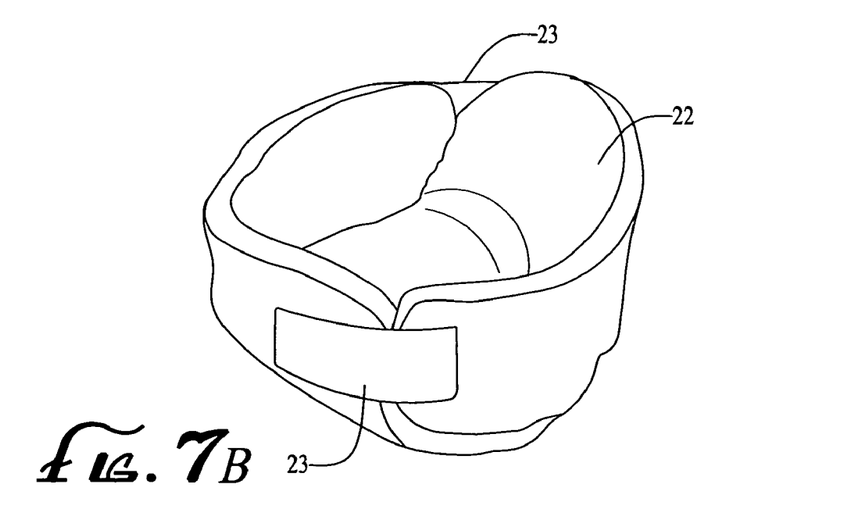
FIG. 7b is a front perspective view of a second version of the reticulated end pad.

A preformed reticulated end pad 22 as shown in FIG. 7a is placed within the distal rigid shell 20. The cup shaped open cellular reticulated foam pad 20 is provided in various sizes and diameters to coincide with internal dimensions of the distal rigid shell 20. The reticulated end pad 20 in combination with the soft end liner 34 provides a soft foam cushion between the stump and the shell 20. Alternatively, rather than a preformed fixed size foam cup as shown in FIG. 7a, the cup can be formed of foam sheet such as shown in FIG. 7b which can be sized to each individual patient and held in that shape by a Velcro® fastener 23. As a further alternative, a urethane foam pad can be employed. This has the advantage of being of a somewhat lower cost. However, if it is of a closed cell construction it will not allow air flow on the distal residual limb. Alternatively, a "temper" foam type pad could be used. This is slow recovery foam that allows good impact dispersion but generally is a much higher density and therefore does not provide as soft padding distally.

To apply the limb guard assembly 10, the patient is placed in a supine position with the knee maintained in full extension. The inner soft liner 18 is wrapped around the limb above the surgical site external to any surgical dressings, shrinker socks, Ace® bandages, or drains which may be in place. The reticulated end pad is placed within the shell 20 and the distal rigid shell 20 and end pad 22 are then applied to the stump and the lower end of the inner soft liner, and these components are held in place using the Velcro® fasteners 32 on the inner liner 18 to provide a smooth interface between the limb and the limb guard assembly 10. The lateral projections 30 on the distal rigid shell 20, extending medially and laterally, are fastened by the Velcro® fasteners 32 onto the inner soft liner 18. The medial and lateral (left and right) struts 14 are applied over the soft liner 18 and adhere to the liner 18 as a result of the Velcro fasteners 24 on the adjacent faces of the struts 14.

Three circumferential strap closures 44 are then placed around the assembly securing it to the limb. A first strap closure 44 is placed at the point where the struts 14 overlap the lateral projections 30 on the rigid shell 20 to secure the struts 14 to the shell 20. The second strap closure 44 is placed directly over the patella to maintain knee extension. The third strap closure 44 is placed at the uppermost proximal edge of the struts 14, securing the struts to the liner 18. The inverted Y suspensor 12 is then fastened to the D rings 28 on the struts 14, preferably at a point approximately 2-4 inches above the superior patella. If not previously secured to the waist belt 42, the Y suspensor 12 is attached to the waist belt and the waist belt is secured around the waist of the patient. As previously indicated, the waist belt can be inverted so it can be used for either a right or left amputation. The waist belt 42 should be fastened so as to provide unrestricted hip range of motion. The waist belt suspensor 16 holds the device in position while the patient is being mobilized or ambulating.

The limb guard assembly 10 can be adjusted to easily accommodate varying thickness surgical dressing by readjusting the tension on the circumferential strap closures 44. Removal of the limb guard assembly 10 is easily accomplished by opening the uppermost proximal and, middle circumferential strap closures 44, opening the waist belt and opening the soft interface wrap 18. To reapply the assembly 10 the process is reversed.

While the limb guard assembly 10 is described with preferred materials of construction and Velcro® fasteners, one skilled in the art will recognize that alternative materials and fastening systems can be used without departing from the teachings herein. Generally speaking, a limb guard assembly incorporating features of the invention includes at least two struts 14 and a distal rigid shell 20, both of which are formed from a relatively stiff structural material. Other components, namely the inner liner 18, the end liner 34 and the end pad 33 are of a soft compliant foam or fabric material, or combination. The waist belt suspensor assembly 16 and the circumferential strap closure 44 may be composed of materials typically used in strapping and retaining prosthetic devices or other devices on to the body of patients.

I claim:

1. A non-load bearing limb guard system for application to a stump remaining following amputation of a portion of a limb said system designed to fit either a left or right limb without interchanging components and to be placed interchangeably over a surgical dressing, a post operative dressing, or a surgical sock, said system comprising:
    a) an inner soft liner for placement on and around the limb above the end of the stump,
    b) an end pad for placement over the stump,
    c) a shell for placement over the end pad and inner soft liner,
    d) a medial strut and a lateral struts each extending laterally along the length of the limb guard system and over and in contact with the inner soft liner, said medial strut and lateral strut each including hook fasteners along an inner surface of each strut for attachment of the struts directly to the inner soft lining,
    e) strap closures for securing the inner soft liner, shell with enclosed end pad and struts to the limb, and
    e) a waist belt and suspensor, the suspensor having a single upwardly extending portion for attachment to the waist band at an upper end and left and right lower portions for attachment directly to the medial and lateral struts respectively.

2. The limb guard system of claim 1 wherein the inner soft liner comprises a sheet of a foam or fabric materials, an outer surface thereof providing attachment structure for receiving the hook fasteners along the inner surface of the strut, said liner also including hook tabs secured along one edge thereof.

3. The limb guard system of claim 1 wherein the end pad comprises a preformed or formable reticulated cup-shaped device with inner dimensions approximating the contour of the stump and outer dimensions sized to fit within the lower end of the shell.

4. The limb guard system of claim 1 wherein the medial and lateral struts are formed from a moldable plastic, a malleable metal or a composite material.

5. A non-load bearing limb guard system for application to the stump remaining following amputation of a portion of a limb said system designed to fit either a left or right limb without interchanging components and to be placed interchangeably over a surgical dressing, a post operative dressing, or a surgical sock, said system comprising:
   a) an inner soft liner for placement on and around the limb above the end of the stump,
   b) an end pad for placement over the stump,
   c) a shell for placement over the end pad and inner soft liner,
   d) medial and lateral struts for placement along the length of the limb and over and in contact with the inner soft liner, said medial and lateral struts including hook fasteners for attachment of the struts directly to the inner soft lining,
   e) strap closures for securing the inner soft liner, shell with enclosed end pad and struts to the limb, and
   e) a waist belt and suspensor, the suspensor having a single upwardly extending portion for attachment to the waist band at an upper end and left and right lower portions for attachment to the medial and lateral struts
wherein the shell is a rigid, conically shaped molded structure larger then but approximating the contour of the stump, said structure having lateral extensions extending upwardly there from, hook attachments on the inner surface of the lateral extensions for attachment of the lateral extensions to the outer surface of the inner soft liner and the outer surface of the lateral extensions having hook or loop attachments thereon, for attachment of compatible fasteners to the outer surface of the lateral extensions.

6. A non-load bearing limb guard system for application to the stump remaining following amputation of a portion of a limb said system designed to fit either a left or right limb without interchanging components and to be placed interchangeably over a surgical dressing, a post operative dressing, or a surgical sock, said system comprising:
   a) an inner soft liner for placement on and around the limb above the end of the stump,
   b) an end pad for placement over the stump,
   c) a shell for placement over the end pad and inner soft liner,
   d) medial and lateral struts for placement along the length of the limb and over and in contact with the inner soft liner, said medial and lateral struts including hook fasteners for attachment of the struts directly to the inner soft lining,
   e) strap closures for securing the inner soft liner, shell with enclosed end pad and struts to the limb, and
   e) a waist belt and suspensor, the suspensor having a single upwardly extending portion for attachment to the waist band at an upper end and left and right lower portions for attachment to the medial and lateral struts
wherein the medial and lateral struts are comprised of a flat, stiff material, said struts having a length approximating the length of the limb guard system, hook fasteners attached to both opposite faces of the struts and along the length thereof, the struts also having structure for attachment of one of the left and right lower portions of the suspensor.

7. A method of protecting the surgical site on a limb following amputation of a portion of the limb comprising
   wrapping an inner liner around the limb above the surgical site,
   placing and end pad within a distal rigid shell and applying the end pad and shell over the stump and the lower end of the soft inner liner,
   securing lateral projections which extend medially and laterally from the distal rigid shell to the inner liner using hook fasteners between the inner soft liner and the lateral projections,
   securing medial and lateral struts longitudinally over the soft liner using hook and loop fasteners between the inner soft liner and each of the medial and lateral struts,
   applying three circumferential strap closures around the assembly securing it to the limb, and
   attaching an inverted Y-shaped suspensor between a waist band and the struts.

8. The method of claim 7 wherein the limb is a leg and a first strap closure is placed at a point where the struts overlap the lateral projections on the rigid shell, securing the struts to the shell, the second strap closure is placed over the patella of the knee to maintain knee extension and the third strap closure is placed at the uppermost proximal edge of the struts, securing the struts to the liner.

9. The method of claim 7 wherein the inverted Y suspensor is fastened to D rings on the struts at a point about 2 to 4 inches above the superior patella.

* * * * *

UNITED STATES PATENT AND TRADEMARK OFFICE
CERTIFICATE OF CORRECTION

PATENT NO. : 7,641,625 B2
APPLICATION NO. : 11/149116
DATED : January 5, 2010
INVENTOR(S) : Ralph W. Nobbe It is certified that error appears in the above-identified patent and that said Letters Patent is hereby corrected as shown below:

- Column 6, Claim 1, Line 53, is written as: d) a medial strut and a lateral struts each extending laterally
It should read as: d) a medial strut and a lateral strut each extending laterally

- Column 6, Claim 2, Line 67, is written as: liner comprises a sheet of a foam or fabric materials, an outer It should read as: liner comprises a sheet of a foam or fabric material, an outer Signed and Sealed this Sixth Day of April, 2010

David J. Kappos
*Director of the United States Patent and Trademark Office*